(12) United States Patent
Elghazaly (10) Patent No.: US 8,273,091 B2
(45) Date of Patent: Sep. 25, 2012

(54) ALIGNMENT DEVICE FOR LOCKING NAIL

(75) Inventor: Timothy M. Elghazaly, Piscataway, NJ (US)

(73) Assignee: EBI, LLC, Parsippany, NJ (US)

( * ) Notice: Subject to any disclaimer, the term of this patent is extended or adjusted under 35 U.S.C. 154(b) by 1109 days.

(21) Appl. No.: 11/867,041

(22) Filed: Oct. 4, 2007

(65) Prior Publication Data

US 2009/0093813 A1 Apr. 9, 2009

(51) Int. Cl.
*A61B 17/58* (2006.01)
*A61B 17/60* (2006.01)
*A61F 2/00* (2006.01)

(52) U.S. Cl. .......................................... 606/96; 606/98
(58) Field of Classification Search .................... 606/96, 606/98, 97
See application file for complete search history.

(56) References Cited

U.S. PATENT DOCUMENTS

| | | | | |
|---|---|---|---|---|
| 2,474,171 | A * | 6/1949 | Ziegner ........................... | 83/762 |
| 2,585,999 | A * | 2/1952 | Bunch ........................... | 242/597.6 |
| 4,881,535 | A * | 11/1989 | Sohngen ........................ | 606/98 |
| 4,983,140 | A | 1/1991 | Gimble | |
| 5,098,383 | A | 3/1992 | Hemmy et al. | |
| 5,178,621 | A * | 1/1993 | Cook et al. ..................... | 606/96 |
| 5,334,192 | A * | 8/1994 | Behrens ......................... | 606/96 |
| 5,346,496 | A | 9/1994 | Pennig et al. | |
| 5,403,321 | A * | 4/1995 | DiMarco ....................... | 606/96 |
| 5,403,322 | A * | 4/1995 | Herzenberg et al. ........... | 606/98 |
| 5,478,341 | A * | 12/1995 | Cook et al. ..................... | 606/62 |
| 6,126,661 | A * | 10/2000 | Faccioli et al. ................. | 606/64 |
| 6,429,013 | B1 | 8/2002 | Halvorsen et al. | |
| 6,555,374 | B1 | 4/2003 | Gimble et al. | |
| 6,841,150 | B2 | 1/2005 | Halvorsen et al. | |
| 7,033,587 | B2 | 4/2006 | Halvorsen et al. | |
| 7,077,847 | B2 * | 7/2006 | Pusnik et al. ................... | 606/96 |
| 7,078,230 | B2 | 7/2006 | Wilkison et al. | |
| 7,078,232 | B2 | 7/2006 | Konkle et al. | |
| 7,144,399 | B2 * | 12/2006 | Hayes et al. .................... | 606/98 |
| 7,588,577 | B2 * | 9/2009 | Fencl et al. ..................... | 606/96 |
| 2003/0009171 | A1 * | 1/2003 | Tornier .......................... | 606/96 |
| 2003/0120280 | A1 * | 6/2003 | Roller et al. .................... | 606/77 |
| 2006/0030859 | A1 | 2/2006 | Gotfried | |
| 2006/0064106 | A1 | 3/2006 | Fernandez | |
| 2006/0106400 | A1 | 5/2006 | Fernandez et al. | |
| 2006/0276911 | A1 * | 12/2006 | Curtis ............................. | 623/38 |

OTHER PUBLICATIONS

TRIGEN™ META-NAIL™ Tibial Nail System, Surgical Techniques. Orthopaedic Trauma & Clinical Therapies. (Feb. 2007). [Brochure]. Smith & Nephew, Inc., Memphis, TN.

* cited by examiner

*Primary Examiner* — Kevin T Truong
*Assistant Examiner* — David Bates
(74) *Attorney, Agent, or Firm* — Harness, Dickey (57) ABSTRACT

An alignment device for an intramedullary locking nail insertable in an intramedullary canal of a long bone. The alignment device includes a locating member having a handle portion connected to an elongated insertion member, and a targeting member movably coupled to the locating member. The insertion member can be inserted in a proximal portion of the intramedullary canal. The targeting member includes a plurality of guiding portions. Each guiding portion is configured to receive one of a plurality of blocking fasteners along an implantation trajectory and into the bone and around the intramedullary canal when the insertion member is inserted into the intramedullary canal. The implantation trajectory of each blocking fastener does not intersect the insertion member.

19 Claims, 6 Drawing Sheets

ALIGNMENT DEVICE FOR LOCKING NAIL

Various intramedullary (IM) locking nails can be used in long bones, such as the tibia, femur, or other bones, to align, stabilize and fix fractures caused by trauma or disease. Locking nails can also be used after osteotomy for fixation of long bones to correct deformity and arthrodesis.

The present teachings provide an alignment device for facilitating the insertion of IM locking nails.

SUMMARY

The present teachings provide an alignment device for an intramedullary locking nail insertable in an intramedullary canal of a long bone. The alignment device includes a locating member having a handle portion connected to an elongated insertion member, and a targeting member movably coupled to the locating member. The insertion member can be inserted in a proximal portion of the intramedullary canal. The targeting member includes a plurality of guiding portions. Each guiding portion is configured to receive one of a plurality of blocking fasteners along an implantation trajectory and into the bone and around the intramedullary canal when the insertion member is inserted into the intramedullary canal. The implantation trajectory of each blocking fastener does not intersect the insertion member.

In another aspect, the alignment device can include a plurality of blocking bone fasteners, an elongated insertion member insertable in a proximal portion of the intramedullary canal, and a targeting member movably coupled to the insertion member selectively in first or second non-parallel orientations. The targeting member includes a plurality of guiding portions defining implantation trajectories for inserting the plurality of bone fasteners transversely through the long bone on diametrically opposite sides along the intramedullary canal, the implantation trajectories not intersecting the insertion member.

In yet another aspect, the alignment device includes a locating member having a handle portion attached to a head portion, and an insertion member extending from the head portion, the head portion defining first and second grooves, and the insertion member insertable in a proximal portion of the intramedullary canal. The alignment device also includes a plurality of blocking fasteners and a targeting member movably coupled to the head portion of the locating member. The targeting member includes first and second portions defining a substantially L-shape, the first portion being substantially parallel to the insertion member and including a plurality of guiding portions. Each guiding portion is configured to receive one of the plurality of blocking fasteners along an implantation trajectory non-intersecting the insertion member when the insertion member is inserted into the intramedullary canal. The second portion of the targeting member includes a protrusion movably insertable in any one of the first or second grooves of the head portion.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although the present teachings are illustrated for use with a tibia, the present teachings can be used for other long bones, such as the femur.

Figure 1:
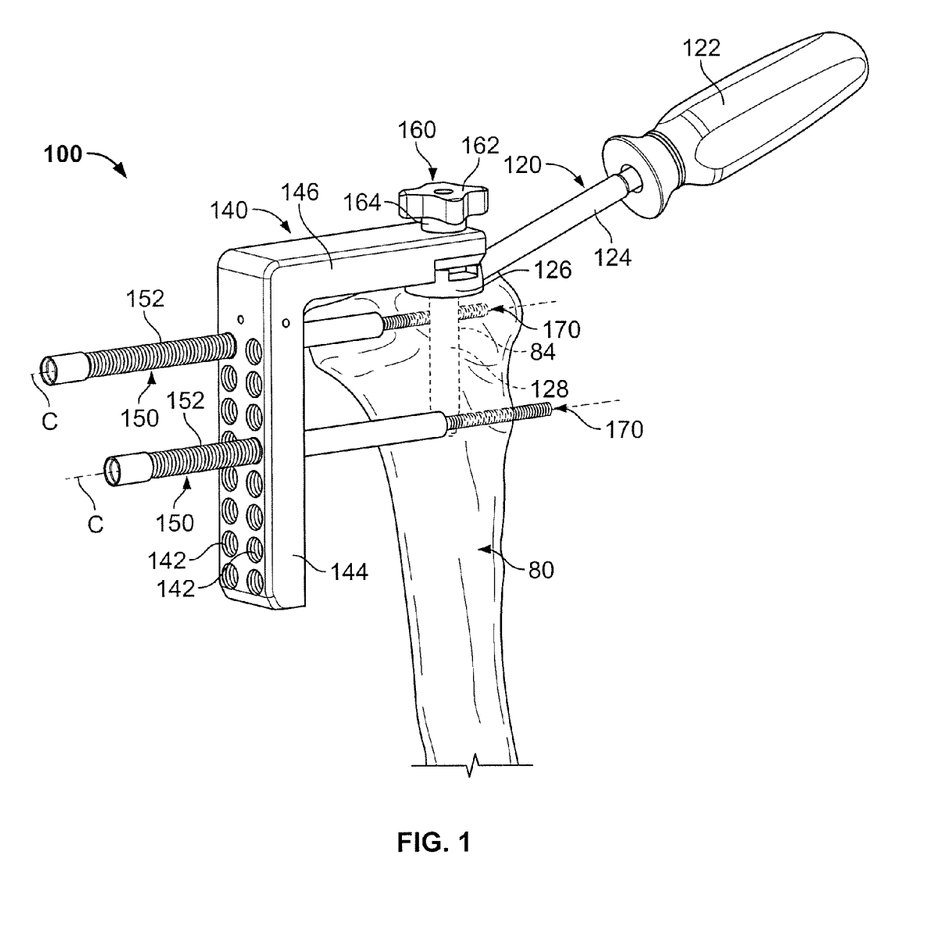
FIG. 1 is a perspective environmental view of an alignment device according to the present teachings, shown in use with a long bone.
Figure 9:
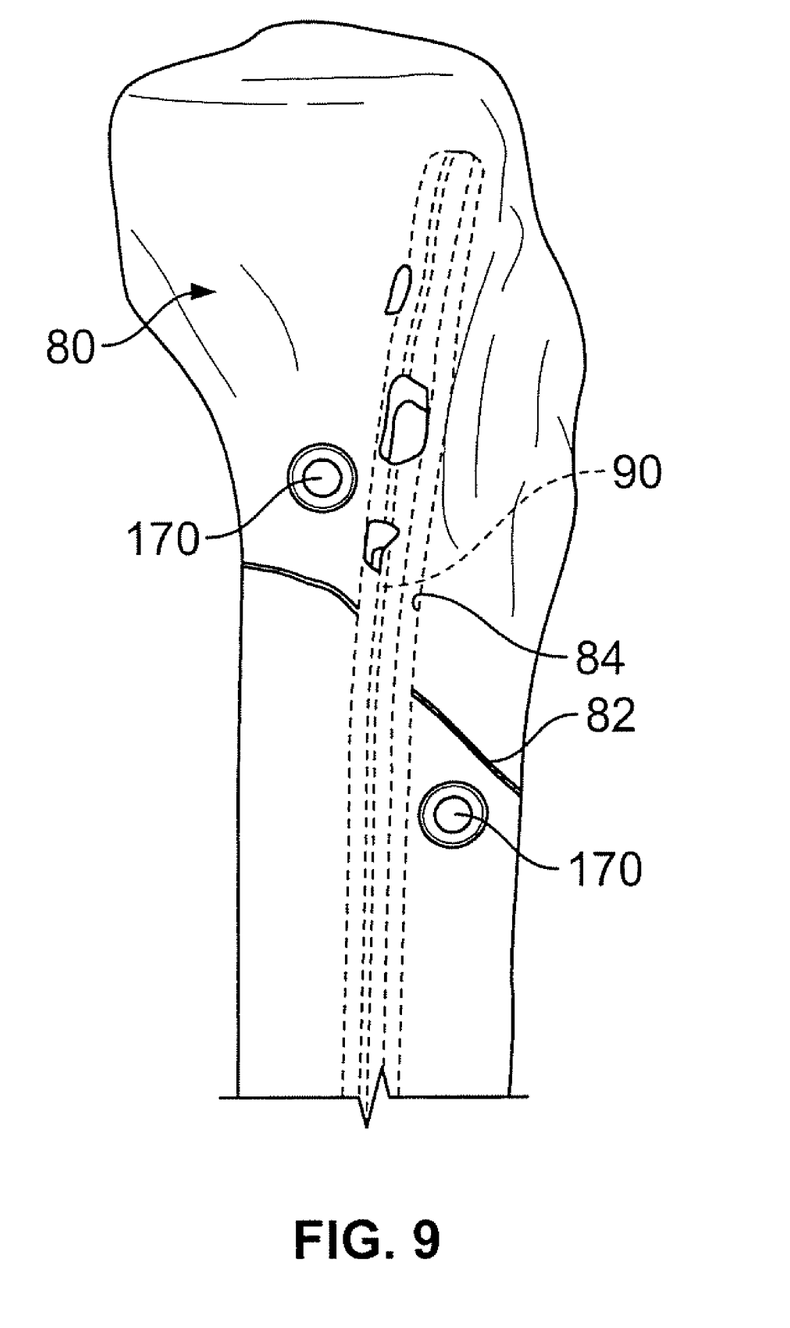
FIG. 9 is an environmental side view of blocking fasteners inserted with alignment device of FIG. 1 for guiding a locking nail.

Referring to FIG. 1, an exemplary alignment device 100 according to the present teachings is illustrated in use with a long bone 80, such as a tibial or femoral bone. The alignment device 100 can be used to insert blocking screws or other bone fasteners 170 on either side of an intramedullary (IM) canal 84 in preparation for guiding the implantation of an IM locking nail 90, as shown in FIG. 9. The blocking fasteners 170 can be implanted along implantation trajectories in the cortical bone in various locations and different planes relative to the IM canal 84 to define a guiding path for the IM locking nail 90, thereby reducing the possibility of displacing bone fragments during nail implantation and also reducing the risk of bone misalignment subsequent to nail implantation.

Referring to FIGS. 1-8, the alignment device 100 can include a locating member 120 and a targeting member 140. The blocking fasteners 170 can be inserted through soft tissue sleeves 150 or other tubular members 150 passing through respective guiding portions 142 of the targeting member 140. The sleeves 150 can include threaded portions 152 that can be threadably engage the guiding portions 142 which can also be threaded. Threadably engaging the sleeves 150 to the guiding portions 142 can be used to provide a controlled compression force the bone 80 by the sleeve 150 and contribute to fracture reduction during use of the alignment device 100. The blocking fasteners 170 can also be inserted directly through the guiding portions 142 without the use of the soft tissue sleeves 150. Each guiding portion 142 can define an implantation trajectory centered about an axis C for guiding a corresponding blocking fastener 170.

Figure 8:
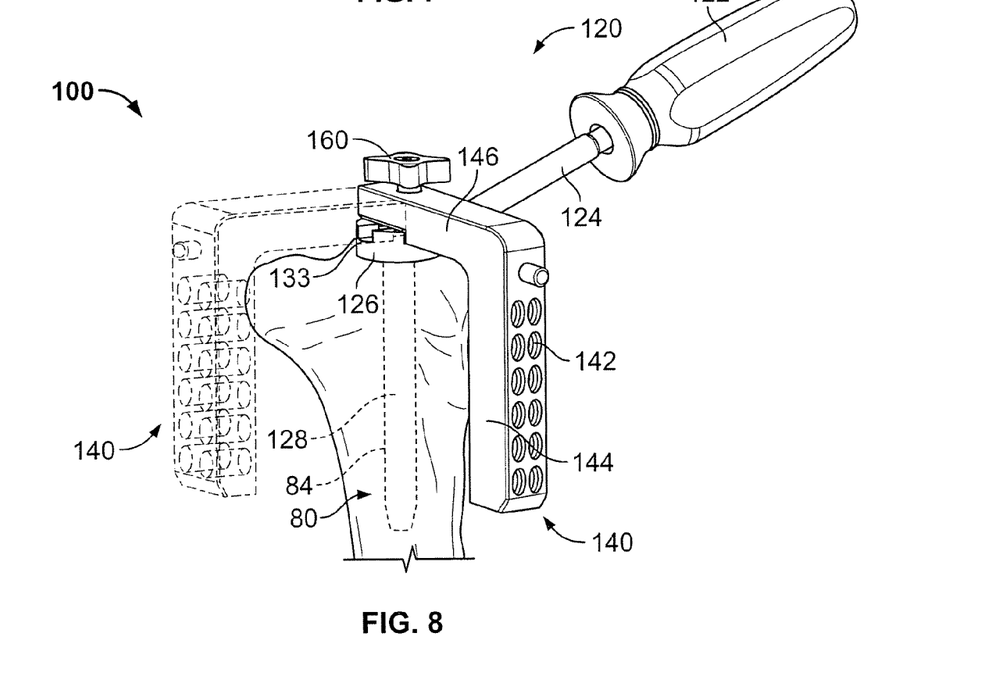
FIG. 8 a perspective environmental view of the alignment device of FIG. 7, shown with the targeting member in a second orientation.

The targeting member 140 can be movably coupled to the locating member 120, as shown in FIG. 8, for inserting blocking fasteners 170 in the anterior/posterior, medial/lateral or other orientations relative to the IM canal 84. For each orientation, the targeting member 140 can be fixed relative to the locating member 120 during the insertion of the blocking fasteners 170 by tightening a thumbscrew or other securing member 160 to prevent relative movement. The securing member 160 can be loosened to permit relative movement between the targeting member 140 and the locating member 120, and allow the targeting member 140 to be moved to another orientation relative to the locating member 120, as discussed below.

Figure 2:
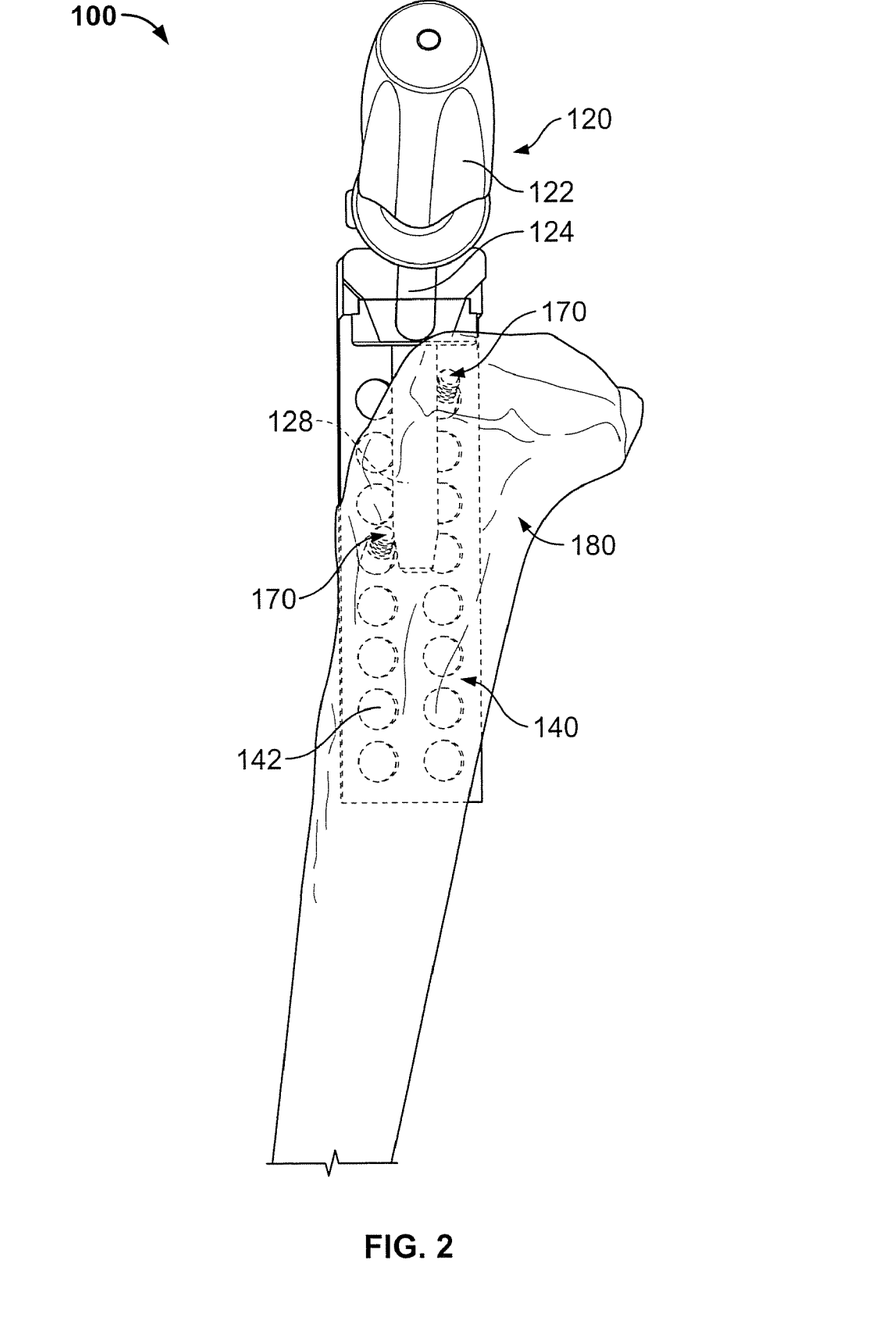
FIG. 2 is a side view of the alignment device of FIG. 1.
Figure 3:
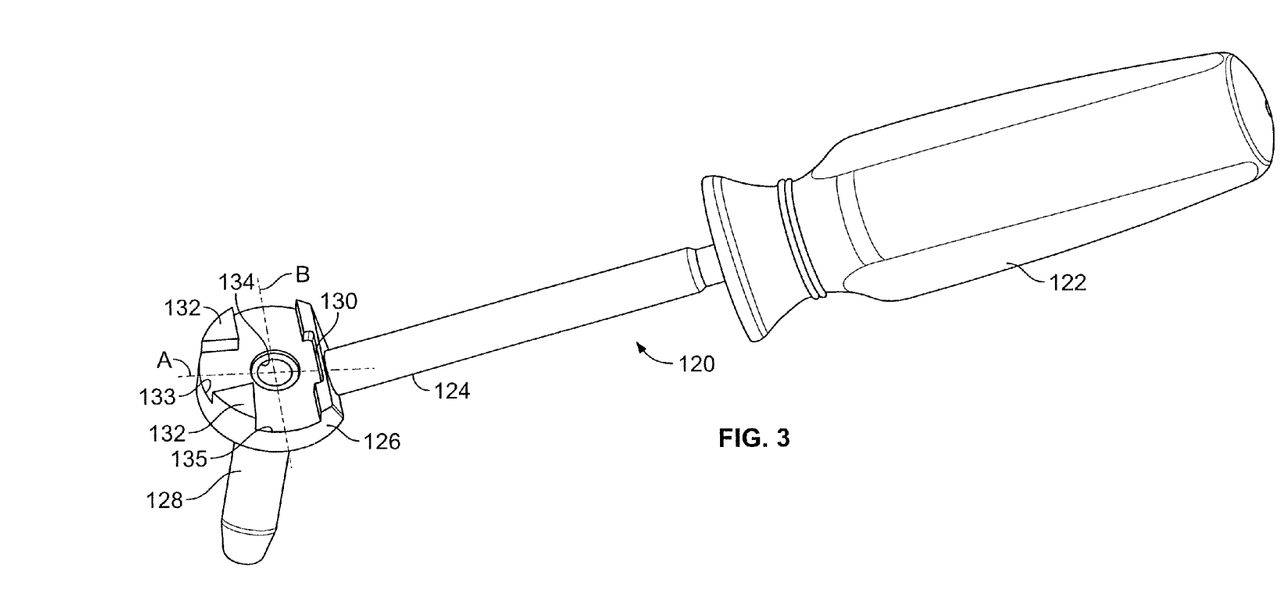
FIG. 3 is a perspective view of a locating member of the alignment device of FIG. 1.
Figure 6:
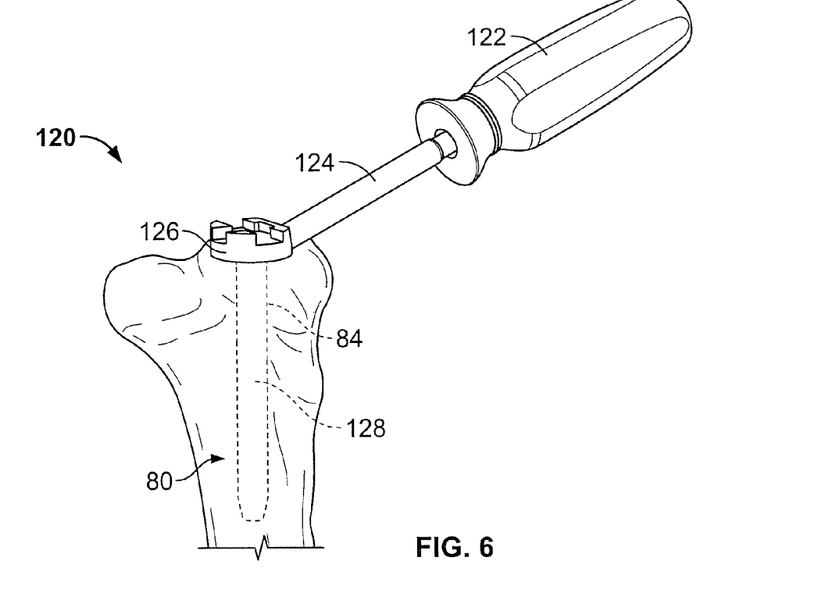
FIG. 6 is a perspective environmental view of the locating member of FIG. 3, shown in use with a long bone.

Referring particularly to FIGS. 2, 3 and 6, the locating member 120 can include a gripping handle 122, and a shaft 124 extending from the handle 122. The shaft 124 can be fixedly attached or modularly coupled with a substantially plate-like head portion 126. An elongated insertion member 128 can extend integrally or modularly from the head portion 126 at an angle appropriate for insertion relative to the shaft 124. The insertion member 128 can substantially replicate the outer shape of the proximal portion of the locking nail 90 for insertion into the IM canal 84, thereby defining a "dummy" nail or a proximal trial nail. The head portion 126 can reside outside the IM canal 84 and above the bone surface, as shown in FIG. 6, when the insertion member 128 is inserted into the IM canal 84. The head portion 126 can be modularly coupled to the targeting member 140, as discussed below.

Figure 4:
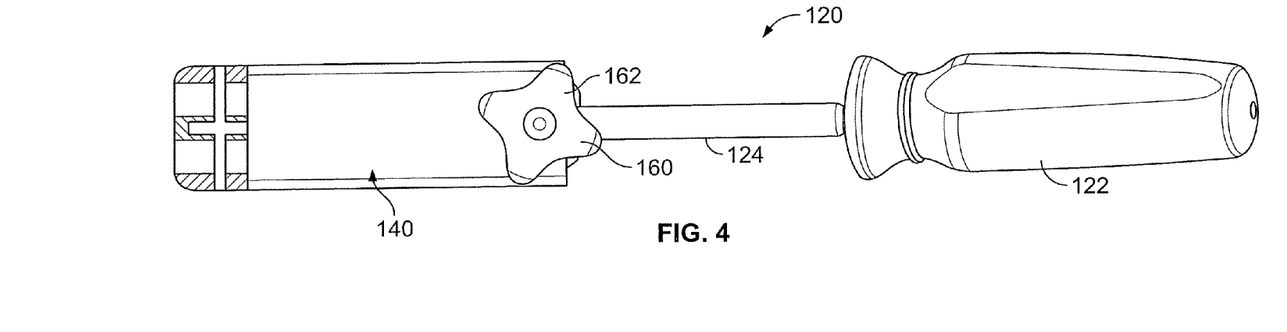
FIG. 4 is a top view of the alignment device of FIG. 2.
Figure 5:
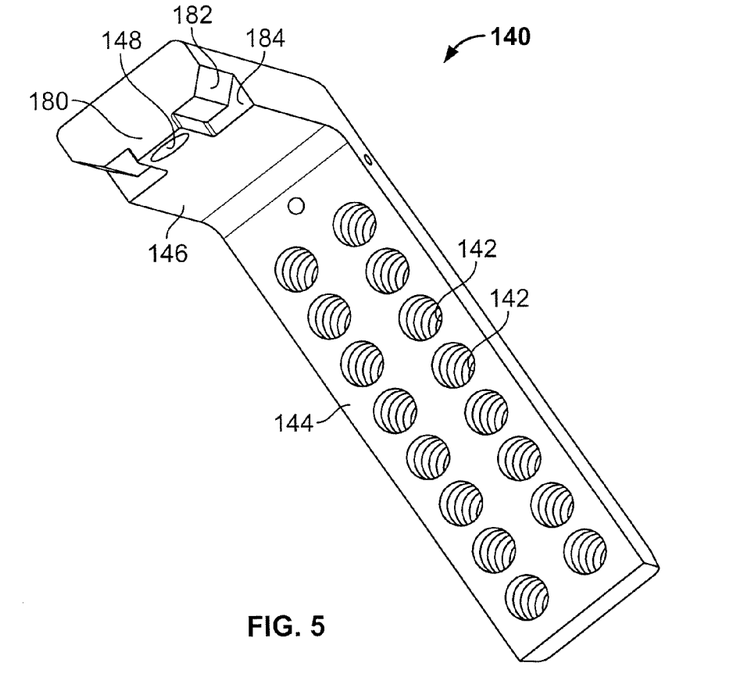
FIG. 5 is a perspective view of a targeting member of the alignment device of FIG. 1.

Referring to FIGS. 1, 4 and 5, the targeting member 140 can be substantially L-shaped and include first and second portions 144, 146 substantially perpendicular to one another. The first portion 144 can be substantially flat or planar, and can include guiding portions 142 arranged for guiding corresponding blocking fasteners 170 into the bone 80. The guiding portions can include a plurality of completely separate guiding apertures, as shown in FIG. 5. Alternatively, the guiding portions 142 can include a pair of elongated slots defining partially communicating guiding apertures. In the illustration of FIG. 5, the guiding portions 142 are shown as distinct and separate circular holes arranged in two spaced-apart columns, such that the blocking fasteners 170 can be inserted on opposite sides of the IM canal 90, for example, in anterior and posterior sides, or medial and lateral sides, as shown in FIG. 9. The implantation trajectories defined by the guiding portions 142 are configured for not intersecting the insertion member 128, when the insertion member 128 is inserted in the IM canal 84, as shown in FIG. 1.

Referring to FIGS. 3 and 5, the second portion 146 of the targeting member 140 can include a sidewall 184 and a protrusion 180 extending from the sidewall 184 and having slanted sides 186. The protrusion 180 is sized and shaped, or generally configured, to slidably engage the head portion 126 of the locating member 120 selectively either along a first track or groove 133 oriented along a first axis A or along a second track or groove 135 oriented along a second axis B. The axes A and B can be substantially perpendicular to one another, corresponding, for example, to anterior-posterior and medial-lateral orientations or other mutually orthogonal orientations. The first and second tracks 133, 135 can be in the form of dovetail grooves formed between various upper surface segments 132, 130 of the head portion 126. The protrusion 180 can have a profile corresponding to the dovetail shape of the tracks 133, 135. It will be appreciated that the locations of the protrusion 180 and tracks 133, 135 can interchanged in an alternate aspect, such that the protrusion 180 is defined on the head portion 126 and the tracks 133, 135 are defined on the targeting member 140.

Referring to FIGS. 1, 3, 5, 7 and 8, the securing member 160 can be used to secure the targeting member 140 in first and second orientations corresponding to the first and second tracks 133, 135. The securing member 160 can include a shaft portion 164 that can pass through corresponding apertures 148, 134 of the targeting member 140 and the locating member 120. The securing member 160 can also include a gripping portion 162 having a thumbscrew formation for manual rotation or other formations for rotation with the help of driver or similar tool.

Figure 7:
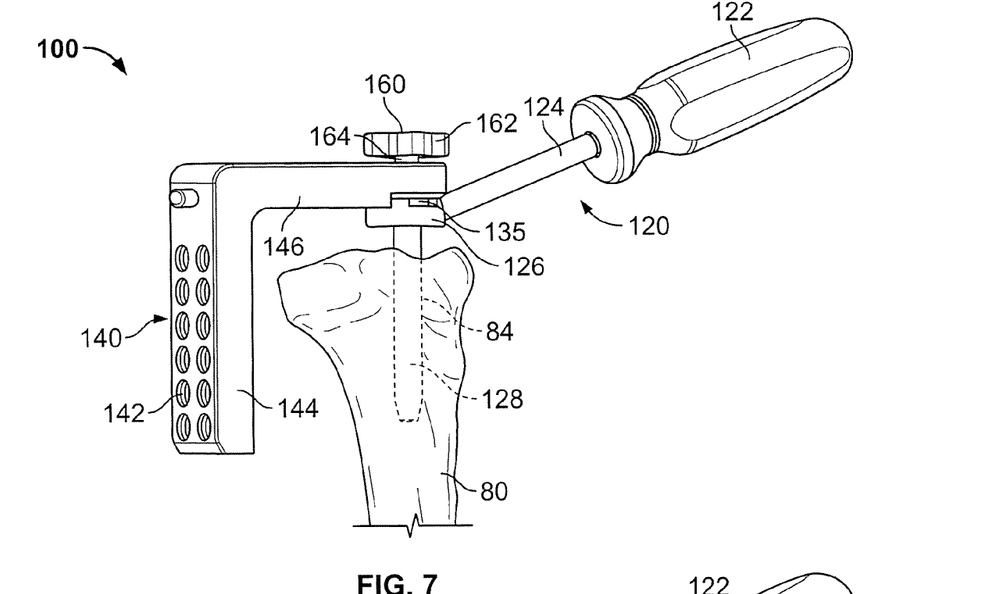
FIG. 7 a perspective environmental view of the alignment device of FIG. 1, shown with the targeting member in a first orientation.

Referring to FIGS. 6-9, an exemplary procedure for using the alignment device 100 is illustrated. The insertion member 128 of the locating member 120 can be inserted into the proximal portion of the IM canal 84, as shown in FIG. 6. The targeting member 140 can be connected to the head portion 126 of the locating member 120, and secured or locked in a first orientation, for example along the first track 133, as shown in FIG. 7, by rotating the securing member 160 in a first rotational direction. A set of blocking fasteners 170 can be inserted transversely into the bone 80 on either side of the IM canal 84 along implantation trajectories defined by the guiding portions 142 and oriented substantially transversely to the IM canal 84, corresponding to the first orientation, as shown, for example in FIG. 1.

The securing member 160 can be rotated in the opposite rotational direction and loosened, such that the targeting member 140 can slightly lifted and swung over to a second orientation, for example along track 135, as shown in FIG. 8. Another set of blocking fasteners 170 can be similarly inserted transversely into the bone 80 and the IM canal 84 on either side of the IM canal 84 along implantation trajectories defined by the guiding portions 142 and corresponding to the second orientation. The IM locking nail 90 can be inserted into the IM canal 84 guided by the blocking fasteners 170 and using known methods of IM nail insertion, such as, for example, the methods described in co-pending application Ser. No. 11/627,575, filed Jan. 26, 2007, and incorporated herein by reference.

Referring to FIG. 9, after the blocking fasteners 170 have been inserted into the bone 80, the securing member 160, the targeting member 140 and the locating member 120 can be removed, leaving in the bone 80 the blocking fasteners 170 along the length of the IM canal 84 and transversely oriented relative to the IM canal 84, and the IM locking nail 90, as shown in FIG. 9. As discussed above, the blocking fasteners 170 can provide an alignment path for the locking nail 90 and prevent varus or valgus and anterior or posterior misalignment of a bone fragment proximally of a fracture 82 of the bone 80.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the present teachings as defined in the following claims.

What is claimed is:

1. An alignment device for an intramedullary locking nail insertable in an intramedullary canal of a long bone, the alignment device comprising:
 a locating member including a handle portion connected to a plate-like head portion integrally formed with an elongated insertion member, the insertion member insertable into a proximal portion of the intramedullary canal to extend along a longitudinal axis prior to the insertion of the intramedullary locking nail;
 a targeting member movably coupled to the head portion of the locating member, the targeting member including a plurality of guiding portions, each guiding portion configured to receive one of a plurality of blocking fasteners along an implantation trajectory to guide the respective one of the plurality of blocking fasteners into the bone and around the intramedullary canal when the insertion member is inserted into the intramedullary canal, the implantation trajectory of each blocking fastener not intersecting the axis of the insertion member.

2. The alignment device of claim 1, further comprising a securing member, the securing member operable to selectively secure the targeting member in one of first or second orientations structurally defined on the head portion of the locating member, the first and second orientations orthogonal to one another.

3. The alignment device of claim 2, wherein the targeting member is coupled to the head portion of the locating member in each of the first and second orientations by a dovetail-type connection.

4. The alignment device of claim 3, wherein the dovetail-type connection includes a protrusion selectively insertable into a first or second dovetail groove.

5. The alignment device of claim 4, wherein the first and second dovetail grooves are defined in the head portion of the locating member.

6. The alignment device of claim 2, in combination with the plurality of blocking fasteners.

7. The alignment device of claim 6, further comprising a plurality of soft tissue sleeves threadably insertable into the guiding portions of the targeting device for receiving corresponding blocking fasteners and compressing the bone.

8. The alignment device of claim 1, wherein the targeting arm includes first and second portions substantially orthogonal to one another.

9. The alignment device of claim 8, wherein the guiding portions are defined in the first portion, and wherein the second portion is movably coupled to the locating member.

10. An alignment device for an intramedullary locking nail insertable in an intramedullary canal of a long bone, the alignment device comprising:
a plurality of blocking bone fasteners;
an elongated insertion member insertable into a proximal portion of the intramedullary canal prior to the insertion of the intramedullary nail so as to extend along an axis, the insertion member having a handle fixedly coupled to the insertion member and extending outwardly at an angle relative to the axis; and
a targeting member movably coupled to the insertion member selectively in first or second non-parallel orientations, the targeting member including a plurality of guiding apertures, the guiding apertures defining implantation trajectories for inserting the plurality of bone fasteners transversely through the long bone on diametrically opposite sides along the intramedullary canal, the implantation trajectories not intersecting the axis of the insertion member.

11. The alignment device of claim 10, further comprising a head portion substantially orthogonal to the insertion member, the head portion defining first and second tracks selectively couplable to a protrusion of the targeting member.

12. The alignment device of claim 11, wherein the first and second tracks define dovetail grooves.

13. The alignment device of claim 11, further comprising a securing member for securing the head portion to the targeting member in each of the first or second orientations.

14. The alignment device of claim 10, wherein the targeting member is substantially L-shaped.

15. The alignment device of claim 10, wherein the first and second orientations correspond to anterior-posterior and medial-lateral orientations.

16. An alignment device for an intramedullary locking nail insertable in an intramedullary canal of a long bone, the alignment device comprising:
a locating member including a handle portion fixedly attached to a plate-like head portion, and an insertion member extending from and integrally formed with the head portion, the head portion defining first and second grooves, the insertion member insertable in a proximal portion of the intramedullary canal prior to the insertion of the intramedullary locking nail so as to extend along an axis, the handle extending at an angle relative to the axis;
a plurality of blocking fasteners; and
a targeting member movably coupled to the head portion of the locating member, the targeting member including first and second portions defining a substantially L-shape, the first portion of the targeting member substantially parallel to the insertion member and including a plurality of guiding portions, each guiding portion configured to receive one of the plurality of blocking fasteners along an implantation trajectory non-intersecting the axis of the insertion member when the insertion member is inserted into the intramedullary canal, the second portion of the targeting member including a protrusion movably insertable in any one of the first or second grooves of the head portion.

17. The alignment device of claim 16, wherein each of the first and second grooves has a dovetail-type shape.

18. The alignment device of claim 16, further comprising a securing screw coupling the head portion of the locating member to the second portion of the targeting device through corresponding openings.

19. The alignment device of claim 16, further comprising a plurality of soft tissue sleeves threadably insertable into the guiding portions of the targeting device for receiving corresponding blocking fasteners and compressing the bone.

* * * * *

UNITED STATES PATENT AND TRADEMARK OFFICE
CERTIFICATE OF CORRECTION

| | | |
|---|---|---|
| PATENT NO. | : 8,273,091 B2 | Page 1 of 1 |
| APPLICATION NO. | : 11/867041 | |
| DATED | : September 25, 2012 | |
| INVENTOR(S) | : Timothy M. Elghazaly | |

It is certified that error appears in the above-identified patent and that said Letters Patent is hereby corrected as shown below:

Column 1,
Line 2, insert --INTRODUCTION--

Column 2,
Line 12, after "FIG. 7" insert --is--

Column 2,
Line 15, after "FIG. 8" insert --is--

Column 2,
Line 48, replace "engage" with --engaged to--

Column 2,
Line 51, after "force" insert --to--

Column 3,
Line 54, after "can" insert --be--

Column 4,
Line 17, after "can" insert --be--

Signed and Sealed this
Twenty-fifth Day of December, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,273,091 B2 | Page 1 of 1 |
| APPLICATION NO. | : 11/867041 | |
| DATED | : September 25, 2012 | |
| INVENTOR(S) | : Elghazaly | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1233 days.

Signed and Sealed this
Twenty-sixth Day of August, 2014

Michelle K. Lee
*Deputy Director of the United States Patent and Trademark Office*